US011060200B2

(12) United States Patent
Tatsumi

(10) Patent No.: US 11,060,200 B2
(45) Date of Patent: Jul. 13, 2021

(54) TIN ALLOY PLATING SOLUTION

(71) Applicant: MITSUBISHI MATERIALS CORPORATION, Tokyo (JP)

(72) Inventor: Koji Tatsumi, Sanda (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 0 days.

(21) Appl. No.: 17/051,570

(22) PCT Filed: Jun. 28, 2019

(86) PCT No.: PCT/JP2019/025888
§ 371 (c)(1),
(2) Date: Oct. 29, 2020

(87) PCT Pub. No.: WO2020/021965
PCT Pub. Date: Jan. 30, 2020

(65) Prior Publication Data
US 2021/0140060 A1 May 13, 2021

(30) Foreign Application Priority Data

Jul. 27, 2018 (JP) .............................. JP2018-141146
Jun. 27, 2019 (JP) .............................. JP2019-119213

(51) Int. Cl.
*C25D 3/60* (2006.01)
*C07C 321/14* (2006.01)

(52) U.S. Cl.
CPC .............. *C25D 3/60* (2013.01); *C07C 321/14* (2013.01)

(58) Field of Classification Search
None
See application file for complete search history.

(56) References Cited

U.S. PATENT DOCUMENTS

| | | | |
|---|---|---|---|
| 6,251,249 B1 | 6/2001 | Chevalier et al. | |
| 6,607,653 B1 | 8/2003 | Tsuji et al. | |
| 8,980,077 B2 * | 3/2015 | Romer | H01L 24/13 |
| | | | 205/238 |
| 2017/0204528 A1 * | 7/2017 | Tsujimoto | C25D 3/58 |

FOREIGN PATENT DOCUMENTS

| | | |
|---|---|---|
| CN | 101194049 A | 6/2008 |
| CN | 102677139 A | 9/2012 |
| CN | 106460215 A | 2/2017 |
| EP | 1069211 A2 | 1/2001 |
| JP | H11-269691 A | 10/1999 |
| JP | 2000-192279 A | 7/2000 |
| JP | 2001 164396 A | 6/2001 |
| JP | 2003-171789 A | 6/2003 |
| JP | 3433291 B2 | 8/2003 |
| JP | 2006-265572 A | 10/2006 |
| JP | 2007-046142 A | 2/2007 |
| JP | 2017-031447 A | 2/2017 |
| TW | 201443294 A | 11/2014 |

OTHER PUBLICATIONS

Office Action dated Dec. 8, 2020, issued for the Taiwanese patent application No. 108124055.
International Search Report dated Sep. 24, 2019, issued for PCT/JP2019/025888 and English translation thereof.
Office Action dated Mar. 23, 2021, issued for Chinese Patent Application No. 201980037541.2 and the English translation of the Search Report.

* cited by examiner

*Primary Examiner* — Wojciech Haske
(74) *Attorney, Agent, or Firm* — Locke Lord LLP

(57) ABSTRACT

A tin alloy plating solution includes a soluble tin salt, a soluble salt of a metal more noble than tin, and a sulfide compound represented by General Formula (1). In the General Formula (1), (A) is a hydrocarbon group including no oxygen atom and having 1 to 2 carbon atoms, or (A) is a hydrocarbon group including one or more oxygen atoms and having 2 to 6 carbon atoms. The metal which is more noble than tin is preferably silver, copper, gold or bismuth.

18 Claims, No Drawings

TIN ALLOY PLATING SOLUTION

TECHNICAL FIELD

The present invention relates to a tin alloy plating solution for forming a tin alloy plating film by an electroplating method. More specifically, the present invention relates to a tin alloy plating solution suitable for forming solder bumps for semiconductor wafers and printed circuit boards.

Priority is claimed on Japanese Patent Application No. 2018-141146, filed in Japan on Jul. 27, 2018 and Japanese Patent Application No. 2019-119213 filed in Japan on Jun. 27, 2019, the content of which are incorporated herein by reference.

BACKGROUND ART

It is known that, in a tin alloy plating bath (solution) used to form a tin alloy plating film, for example, a tin-silver alloy plating film, on a conductive object, in a case where the redox potentials of the tin ions and the other metal ions (for example, silver ions) in the bath are significantly different, metal ions which are more noble than tin form insoluble salts or metal simple substances in the plating bath which precipitate easily and it is difficult to stably maintain the plating bath. For this reason, in the related art, a plating solution containing a cyanide compound was used as a tin-silver alloy plating solution, for example. However, since this bath contains a toxic cyanide compound, the bath is extremely toxic and there are various problems in terms of handling.

As a tin alloy plating bath which does not contain a cyanide compound, various plating baths (solutions) were proposed (refer to, for example, Patent Documents 1 to 4) in the related art. Patent Document 1 illustrates a non-cyanide-based stable silver and silver alloy plating bath and this silver and silver alloy plating bath contains (A) a soluble salt consisting of any of a silver salt or a mixture of a silver salt and a salt of a metal such as tin, bismuth, indium, or lead, and (B) a specific sulfide-based compound such as 2,2'-dipyridyl sulfide or 2,2'-dipiperazinyl disulfide having one or more basic nitrogen atoms in the molecule or a specific thiocrown ether compound such as 1-aza-7-oxa-4,10-dithiacyclododecane. This plating bath containing these specific compounds makes the aging stability of the plating bath, the co-deposition of silver and various metals, the appearance of the electrodeposition coating, and the like excellent in comparison with baths containing other sulfur-based compounds such as thioglycolic acid.

Patent Document 2 illustrates a non-cyanide-based stable silver and silver alloy plating bath and this silver and silver alloy plating bath contains (A) a soluble salt consisting of any of a silver salt or a mixture of a silver salt and a salt of a metal such as tin, bismuth, indium, or lead, and (B) a specific aliphatic sulfide-based compound such as thiobis (diethylene glycol), dithiobis(triglycerol), 3,3'-thiodipropanol, and thiodiglycerin, which include one or more of an etheric oxygen atom, a 1-hydroxypropyl group, or a hydroxypropylene group in the molecule but which do not include a basic nitrogen atom. According to this plating bath, containing these specific compounds makes the aging stability of the plating bath, the co-deposition of silver and various metals, the appearance of the electrodeposition coating, and the like excellent in comparison with a bath or the like containing a thiodiglycolic acid or β-thiodiglycol, which are aliphatic monosulfide compounds which do not include an etheric oxygen atom, a 1-hydroxypropyl group, or a hydroxypropylene group.

Patent Document 3 illustrates a non-cyanide-based tin-silver alloy plating bath and this tin-silver alloy plating bath contains (a) at least one type of aliphatic amino acid and nitrogen-containing aromatic carboxylic acid and (b) at least one type of aliphatic sulfide and aliphatic mercaptan. Examples of the aliphatic amino acids of (a) include glycine and the like, examples of the nitrogen-containing aromatic carboxylic acids of (a) include picolinic acid, 3-aminopyrazine-2-carboxylic acid, and the like, examples of the aliphatic sulfides of (b) include 4,7-dithiadecane-1,10-diol, and the like, and examples of the aliphatic mercaptans include thioglycol, and the like. In this plating bath, the sulfur compound of component (b) is a silver stabilizer and component (a) such as glycine and picolinic acid is also used in combination therewith to make it possible to favorably improve the solder wettability and appearance of the tin-silver alloy coating.

Patent Document 4 illustrates a cyanide-free, silver-based plating bath, and this plating bath contains a soluble salt including a silver salt and one or more types of sulfide-based compounds selected from a group formed of compounds represented by a particular General Formula. According to this plating bath, it is possible to improve the stability of silver ions in the bath, obtain a sufficient complexing power, and reduce production costs, and the plating bath is excellent in practical use.

CITATION LIST

Patent Literature

[Patent Document 1]
    Japanese Unexamined Patent Application, First Publication No. H11-269691 (Abstract)
[Patent Document 2]
    Japanese Unexamined Patent Application, First Publication No. 2000-192279 (Abstract)
[Patent Document 3]
    Japanese Unexamined Patent Application, First Publication No. 2006-265572 (Abstract)
[Patent Document 4]
    Japanese Unexamined Patent Application, First Publication No. 2007-046142 (Abstract)

SUMMARY OF INVENTION

Technical Problem

The plating baths of Patent Documents 1 to 4 described above contain various complexing agents for forming a silver complex for the stability of silver ions in the plating bath or the aging stability of the plating bath. However, the complexing agents shown in Patent Document 1 to 4 have a problem in that, when the plating bath is used for a long period of time or the plating solution is stored for a long period of time, decomposition occurs and the silver is likely to precipitate.

An object of the present invention is to provide a tin alloy plating solution having excellent electrolytic stability and aging stability.

Solution to Problem

The present inventors conducted extensive studies in order to solve the problems described above and, as a result, found that, when a specific sulfide compound was contained in a tin alloy plating solution, a complex of a metal which is more noble than tin in the plating solution was stabilized without being decomposed either during use or during storage, thereby achieving the present invention.

A first aspect of the present invention is a tin alloy plating solution including a soluble tin salt, a soluble salt of a metal which is more noble than tin, and a sulfide compound represented by General Formula (1). Here, in the General Formula (1), (A) is a hydrocarbon group including no oxygen atom and having 1 to 2 carbon atoms, or (A) is a hydrocarbon group including one or more oxygen atoms and having 2 to 6 carbon atoms.

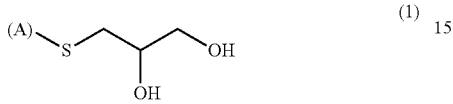
(1)

A second aspect of the present invention is a tin alloy plating solution including a soluble tin salt, a soluble salt of a metal which is more noble than tin, and a sulfide compound represented by General Formula (2). Here, in the General Formula (2), (B) is a hydrocarbon chain including no oxygen atom and having 1 to 4 carbon atoms, or (B) is a hydrocarbon chain including one or more oxygen atoms and having 3 to 4 carbon atoms.

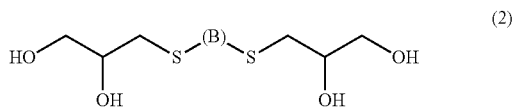
(2)

A third aspect of the present invention is a tin alloy plating solution including a soluble tin salt, a soluble salt of a metal which is more noble than tin, and a sulfide compound represented by General Formula (3). Here, in the General Formula (3), n is 1 to 5.

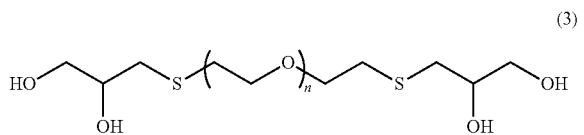
(3)

A fourth aspect of the present invention is the tin alloy plating solution according to any one of the first to third aspects in which the metal which is more noble than tin is at least one or more metals selected from silver, copper, gold, and bismuth.

A fifth aspect of the present invention is the tin alloy plating solution according to any one of the first to fourth aspects, further including at least one or more types of auxiliary complexing agent selected from a gluconic acid or a salt thereof, a citric acid or a salt thereof, a pyrophosphoric acid or a salt thereof, an ethylenediamine, a thiourea, a mercaptothiazole, a mercaptotriazole, a mercaptotetrazole, and a hydroxyalkylphosphine.

A sixth aspect of the present invention is the tin alloy plating solution according to any one of the first to fifth aspects, further including at least one or more types of surfactant selected from an anionic surfactant, a cationic surfactant, a non-ionic surfactant, and an amphoteric surfactant.

A seventh aspect of the present invention is the tin alloy plating solution according to any one of the first to sixth aspects, further including an antioxidant.

An eighth aspect of the present invention is the tin alloy plating solution according to any one of the first to seventh aspects, further including a complexing agent for tin.

A ninth aspect of the present invention is the tin alloy plating solution according to any one of the first to eighth aspects, further including a pH adjusting agent.

A tenth aspect of the present invention is the tin alloy plating solution according to any one of the first to ninth aspects, further including a brightening agent.

Advantageous Effects of Invention

In the tin alloy plating solution of the first aspect of the present invention, the sulfide compound acts as a complexing agent for a metal which is more noble than tin in General Formula (1). In a case where (A) is a hydrocarbon group including no oxygen atom and having 1 to 2 carbon atoms, the water solubility of the sulfide compound is good. In addition, in a case where (A) is a hydrocarbon group including one or more oxygen atoms and having 2 to 6 carbon atoms, an ether group "—O—" or a hydroxyl group "—OH" is included in the molecule as an oxygen atom, thus, these act as a hydrophilic group and the sulfide compound has good water solubility due to hydrogen bonding with water. Furthermore, in both cases, since the sulfide group "—S—" is included as a sulfur atom in General Formula (1), it is possible for the S atom to sufficiently form a complex with and stabilize metal ions which are more noble than tin in the plating solution. Due to this, the tin alloy plating solution is excellent in electrolytic stability and aging stability for a long period of time during use and during storage. In addition, since the sulfide compound is appropriately adsorbed on the surface of the plating electrode, in a case where a surfactant is also used in combination therewith as a smoothing agent, this does not interfere with the action of the surfactant and the appearance and film thickness uniformity of the plating film are good.

In the tin alloy plating solution of the second aspect of the present invention, the sulfide compound acts as a complexing agent for a metal which is more noble than tin in General Formula (2). In a case where (B) is a hydrocarbon group including no oxygen atom and having 1 to 4 carbon atoms, the water solubility of the sulfide compound is good. In addition, in a case where (B) is a hydrocarbon group including one or more oxygen atoms and having 3 to 4 carbon atoms, since a hydroxyl group "—OH" is included, this acts as a hydrophilic group and there is an effect of further increasing the water solubility due to hydrogen bonding with water. Furthermore, since the sulfide group "—S—" is included as the sulfur atom in General Formula (2), it is possible for the S atom to sufficiently form a complex with and stabilize the metal ions which are more noble than tin in the plating solution. Due to this, the tin alloy plating solution is excellent in electrolytic stability and aging stability for a long period of time during use and during storage. In addition, since the sulfide compound is appropriately adsorbed on the surface of the plating electrode, in a case where a surfactant is also used in combination therewith as a smoothing agent, this does not interfere with the action of the surfactant and the appearance and film thickness uniformity of the plating film are good.

In the tin alloy plating solution of the third aspect of the present invention, the sulfide compound acts as a complexing agent for a metal which is more noble than tin in General Formula (3). The sulfide compound represented by General Formula (3) has a glyceryl group having excellent water solubility at both ends, and further has 1 to 5 ethylene oxide groups which have the effect of increasing water solubility, thus, the water solubility of the sulfide compound is good due to hydrogen bonding with water. Furthermore, since the S atom is included in General Formula (3), it is possible for the S atom to sufficiently form a complex with and stabilize the metal ions which are more noble than tin in the plating solution. Due to this, the tin alloy plating solution is excellent in electrolytic stability and aging stability for a long period of time during use and during storage. In addition, since the sulfide compound is appropriately adsorbed on the surface of the plating electrode, in a case where a surfactant is also used in combination therewith as a smoothing agent, this does not interfere with the action of the surfactant and the appearance and film thickness uniformity of the plating film are good.

In the tin alloy plating solution of the fourth aspect of the present invention, the metal which is more noble than tin is at least one or more types selected from silver, copper, gold, and bismuth, thus, the solder wettability, mounting strength, bendability, and reflow property are excellent, and there is an effect due to which whisker formation is difficult and the like.

In the tin alloy plating solution of the fifth aspect of the present invention, an auxiliary complexing agent such as gluconic acid or a salt thereof is included, thus, when used together with the sulfide compound of the first to third aspects, it is possible to further improve the stability of the plating solution during use and during storage.

The tin alloy plating solution of the sixth aspect of the present invention further includes a surfactant such as an anionic surfactant, a cationic surfactant, a non-ionic surfactant, an amphoteric surfactant, thus, there is an effect of further improving the external appearance and the film thickness uniformity of the plating film.

The tin alloy plating solution of the seventh aspect of the present invention further includes an antioxidant, thus, there is an effect of preventing $Sn^{2+}$ oxidation in the tin alloy plating solution.

The tin alloy plating solution of the eighth aspect of the present invention further includes a complexing agent for tin, thus, in a case where the tin alloy plating solution is applied to a tin plating solution close to neutral, there is an effect of stabilizing the $Sn^{2+}$ ions.

The tin alloy plating solution of the ninth aspect of the present invention further includes a pH adjusting agent, thus, there is an effect of adjusting the tin alloy plating solution to an arbitrary pH range such as acidic, weakly acidic, or neutral.

The tin alloy plating solution of the tenth aspect of the present invention further includes a brightening agent, thus, there is an effect of refining the crystal particles of the tin alloy in the tin alloy plating film.

DESCRIPTION OF EMBODIMENTS

A description will be given below of the tin alloy plating solutions of the first, second, and third embodiments of the present invention. These tin alloy plating solutions are used as a material for forming a tin alloy plating film used as a solder bump for a semiconductor substrate (wafer) or a printed circuit board, or the like.

In addition, the tin alloys formed of the tin alloy plating solutions of the first, second, and third embodiments are alloys of tin (Sn) and a predetermined metal selected from silver (Ag), copper (Cu), gold (Au), and bismuth (Bi), which are metals more noble than tin, and examples thereof include binary alloys such as an SnAg alloy, an SnCu alloy, an SnAu alloy, and an SnBi alloy, and ternary alloys such as an SnCuAg alloy.

First Embodiment

The tin alloy plating solution of the first embodiment includes a soluble tin salt, a soluble salt of a metal which is more noble than tin, and the sulfide compound represented by General Formula (1). This tin alloy plating solution may further include an additive.

[Soluble Tin Salt]

The soluble tin salt used in the tin alloy plating solution of the first embodiment is a salt which dissolves in water to form divalent tin ions. Examples of soluble tin salts include halides, sulfates, oxides, alkane sulfonates, aryl sulfonates, and alkanol sulfonates. Specific examples of the alkane sulfonate include methane sulfonate and ethane sulfonate. Specific examples of the aryl sulfonate include benzene sulfonate, phenol sulfonate, cresol sulfonate, and toluene sulfonate. Specific examples of the alkanol sulfonate include isethionate.

The soluble tin salt may be used alone as one type or in a combination of two or more types. The amount of the soluble tin salt in the tin alloy plating solution of the first embodiment is, in terms of the amount of tin, preferably in a range of 5 g/L or more and 200 g/L or less, and more preferably 20 g/L or more and 100 g/L. In a case where the amount of the soluble tin salt is excessively low, there is a concern that it may be difficult for the precipitation of tin to occur normally and the formation of good bumps may not be possible in the current density range of 1 to 20 amperes per square decimeter (ASD) generally used in bump plating. On the other hand, in a case where the amount of the soluble tin salt is excessively high, in addition to the increase in the viscosity of the plating solution making it difficult to form bumps, there is a concern that the cost of the plating solution may increase since more tin than necessary is contained.

[Soluble Salts of Metals More Noble than Tin]

The soluble salt of a metal which is more noble than tin used in the tin alloy plating solution of the first embodiment is a salt which is soluble in water. Examples of the metals which are more noble than tin include at least one or more metals selected from silver, copper, gold, and bismuth. Examples of soluble salts of these metals are the same as the examples of soluble tin salts. Among these metals, it is preferable to include silver or copper. An alloy (SnAg alloy) of tin and silver has a low melting point of 221° C. as a eutectic composition (Sn-3.5 wt % Ag), and an alloy (SnCu alloy) of tin and copper has a low melting point of 227° C. as a eutectic composition (Sn-1.7 wt % Cu) and both are excellent in the solder wettability, mounting strength, bendability, and reflow property, and have advantages in that whiskers are not easily formed and the like. The soluble salt of a metal which is more noble than tin may be used alone as one type or in a combination of two or more types. The amount of the soluble salt of a metal which is more noble than tin in the plating solution of the first embodiment is, in terms of the amount of metal, preferably in a range of 0.01 g/L or more and 10 g/L or less, and more preferably in a range of 0.1 g/L or more and 2 g/L or less. In a case where the amount of the soluble salt of a metal which is more noble than tin is excessively low or excessively high, it is not possible for the composition of the solder alloy which precipitates to be a eutectic composition, and it is not possible to obtain the properties as a solder alloy.

[Sulfide Compound represented by General Formula (1)]

The sulfide compound used in the tin alloy plating solution of the first embodiment is represented by General Formula (1) and acts as a complexing agent for the metal which is more noble than tin. This sulfide compound is obtained by mixing α-thioglycerol as a main raw material with, for example, a basic aqueous solution of sodium hydroxide, sodium hydrogen carbonate, or sodium carbonate, then mixing and stirring the auxiliary raw materials described below, and then carrying out refluxing to subject the main raw material and the auxiliary raw materials to a nucleophilic substitution reaction. A method for producing the sulfide compound of Example 3 described below will be illustrated. 100 mL of pure water and 100 mL of ethanol as a solvent are prepared in a 1 L eggplant-shaped flask and 40 g of sodium hydroxide is dissolved therein while stirring. After cooling the solution to 25° C., 108 g of α-thioglycerol is added thereto and mixed therewith. Then, 80 g of 2-chloroethanol is added as an auxiliary raw material and mixed therewith. After refluxing at 80° C. for 18 hours, the solvent is removed by distillation to obtain a sulfide compound represented by Structural Formula (1-3) described below.

Examples of the auxiliary raw material for producing the sulfide compound of the first embodiment include chloromethane, chloroethane, 2-chloroethanol, 3-chloro-1-propanol, 1-chloro-3-metaoxypropane, 3-chloro-1,2-propanediol, 2-(2-chloroethoxy)ethanol, 1-chloro-3-methoxy-2-propanol, 2-[2-(2-chloroethoxy)ethoxy]ethanol, dimethylchloroacetal, 4-chloro-1,2-dihydroxybenzene, and the like.

[Additive]

The tin alloy plating solution of the first embodiment may further include an additive such as an acid electrolyte (free acid), an auxiliary complexing agent, a surfactant, an antioxidant, a complexing agent for tin, a pH adjusting agent, and a brightening agent.

(Acid Electrolyte)

Examples of the acid electrolyte include hydrogen chloride, hydrogen bromide, sulfuric acid, alkane sulfonic acid, aryl sulfonic acid, or alkanol sulfonic acid. Specific examples of the alkane sulfonic acid include methane sulfonic acid and ethane sulfonic acid. Specific examples of the aryl sulfonic acid include benzene sulfonic acid, phenol sulfonic acid, cresol sulfonic acid, and toluene sulfonic acid. Specific examples of the alkanol sulfonic acid include isethionic acid. The acid electrolyte has a function of increasing the conductivity of the tin alloy plating solution.

The acid electrolytes may be used alone as one type or in a combination of two or more types. The amount of the acid electrolyte in the tin alloy plating solution of the first embodiment is preferably in a range of 5 g/L or more and 500 g/L or less, and more preferably in a range of 30 g/L or more and 300 g/L or less.

(Auxiliary Complexing Agent)

Examples of the auxiliary complexing agent include gluconic acid or a salt thereof, citric acid or a salt thereof, pyrophosphoric acid or a salt thereof, ethylenediamines, thioureas, mercaptothiazoles, mercaptotriazoles, mere aptotetrazoles, or hydroxyalkylphosphines. The auxiliary complexing agent may be used alone as one type or in a combination of two or more types.

(Surfactant)

The tin alloy plating solution of the first embodiment preferably contains a surfactant. The surfactant acts to increase the affinity between the tin alloy plating solution and the object to be plated and, by being adsorbed on the surface of the plating film during the formation of the tin alloy plating film to suppress crystal growth of the tin alloy in the plating film so as to refine the crystals, acts to improve the appearance of the plating film, improve the adhesion to the object to be plated, make the film thickness uniform, and the like. As the surfactant, it is possible to use various surfactants such as anionic surfactants, cationic surfactants, non-ionic surfactants, and amphoteric surfactants.

Specific examples of the anionic surfactant include alkyl sulfate, polyoxyethylene alkyl ether sulfate, polyoxyethylene alkylphenyl ether sulfate, alkylbenzene sulfonate, alkylnaphthalene sulfonate, and the like. Specific examples of the cationic surfactant include mono- to tri-alkylamine salts, dimethyldialkylammonium salts, trimethylalkylanunonium salts, and the like. Specific examples of non-ionic surfactant include surfactants or the like in which 2 to 300 mol of ethylene oxide (EO) and/or propylene oxide (PO) are addition-condensed with alkanols, phenols, naphthols, and bisphenols having 1 to 20 carbon atoms, alkylphenols and arylalkylphenols having 1 to 25 carbon atoms, alkylnaphthols having 1 to 25 carbon atoms, alkoxyl phosphoric acid (salt), sorbitan ester, and polyalkylene glycol having 1 to 25 carbon atoms, aliphatic amide having 1 to 22 carbon atoms, and the like. Specific examples of amphoteric surfactants include carboxybetaine, imidazoline betaine, aminocarboxylic acid, and the like.

The surfactants may be used alone as one type or in a combination of two or more types. The amount of the surfactant in the tin alloy plating solution of the first embodiment is generally in a range of 0.01 g/L or more and 50 g/L or less, preferably in a range of 0.1 g/L or more and 20 g/L or less, and more preferably in a range of 1 g/L or more and 10 g/L or less.

(Antioxidant)

It is possible for the tin alloy plating solution of the first embodiment to contain an antioxidant as necessary. The antioxidant has an object of preventing oxidation of $Sn^{2+}$ in the tin alloy plating solution. Examples of antioxidants include ascorbic acid or a salt thereof, pyrogallol, hydroquinone, phloroglucinol, trihydroxybenzene, catechol, cresol sulfonic acid or a salt thereof, catechol sulfonic acid or a salt thereof, hydroquinone sulfonic acid or a salt thereof, and the like. For example, hydroquinone sulfonic acid or a salt thereof is preferable in an acidic bath, while ascorbic acid, a salt thereof, or the like is preferable in a neutral bath.

The antioxidants may be used alone as one type or in a combination of two or more types. The amount of the antioxidant in the tin alloy plating solution of the first embodiment is generally in the range of 0.01 g/L or more and 20 g/L or less, preferably in the range of 0.1 g/L or more and 10 g/L or less, and more preferably is in the range of 0.1 g/L or more and 5 g/L or less.

(Complexing Agent for Tin)

It is possible to apply the tin alloy plating solution of the first embodiment to a tin alloy plating solution of any pH range such as acidic, weakly acidic, and neutral. $Sn^{2+}$ ions are stable in strong acidity (pH: <1), but white precipitates are easily generated in the vicinity of acidity to neutrality (pH: 1 to 7). For this reason, in a case where the tin alloy plating solution of the first embodiment is applied to a tin plating solution which is near neutrality, it is preferable to add a complexing agent for tin for the purpose of stabilizing $Sn^{2+}$ ions.

It is possible to use oxycarboxylic acid, polycarboxylic acid, and monocarboxylic acid as the complexing agent for tin. Specific examples include gluconic acid, citric acid, glucoheptonic acid, gluconolactone, acetic acid, propionic acid, butyric acid, ascorbic acid, oxalic acid, malonic acid, succinic acid, glycolic acid, malic acid, tartaric acid, or salts thereof, and the like. Gluconic acid, citric acid, glucoheptonic acid, gluconolactone, glucoheptolactone, and salts thereof are preferable. In addition, polyamines and aminocarboxylic acids such as ethylenediamine, ethylenediaminetetraacetic acid (EDTA), diethylenetriaminepentaacetic acid (DTPA), nitrilotriacetic acid (NTA), iminodiacetic acid (IDA), iminodipropionic acid (IDP), hydroxyethylethylenediaminetriacetic acid (HEDTA), triethylene tetramine hexaacetic acid (TTNA), ethylenedioxybis(ethylamine)-N, N,N',N'-tetraacetic acid, mercaptotriazoles, mercaptotetrazoles, glycines, nitrilotrimethylphosphonic acid, 1-hydroxyethane-1,1-diphosphonic acid or salts thereof are also effective as complexing agents.

The complexing agent for tin may be used alone as one type or in a combination of two or more types. The amount of the complexing agent for tin in the tin alloy plating solution of the first embodiment is generally in a range of 0.001 mol or more and 10 mol or less with respect to 1 mol of tin in the soluble tin salt compound included in the tin alloy plating solution, preferably in the range of 0.01 mol or more and 5 mol or less, and more preferably in the range of 0.5 mol or more and 2 mol or less.

(pH Adjusting Agent)

It is possible for the tin alloy plating solution of the first embodiment to contain a pH adjusting agent as necessary. Examples of pH adjusting agents include various acids such as hydrochloric acid and sulfuric acid, various bases such as aqueous ammonia, potassium hydroxide, sodium hydroxide, and sodium hydrogen carbonate, and the like. In addition, as the pH adjusting agent, monocarboxylic acids such as acetic acid and propionic acid, dicarboxylic acids such as boric acid, phosphoric acid, oxalic acid, and succinic acid, oxycarboxylic acids such as lactic acid and tartaric acid, and the like are also effective.

(Brightening Agent)

It is possible for the tin alloy plating solution of the first embodiment to contain a brightening agent as necessary. An aromatic carbonyl compound is effective as a brightening agent. The aromatic carbonyl compound has a function of refining the crystal particles of the tin alloy in the tin alloy plating film. The aromatic carbonyl compound is a compound in which a carbonyl group (—CO—X: here, X means a hydrogen atom, a hydroxy group, an alkyl group in which the carbon atoms are in a range of 1 to 6, or an alkoxy group in which the carbon atoms are in a range of 1 to 6) is bonded to carbon atoms of an aromatic hydrocarbon. Aromatic hydrocarbons include benzene rings, naphthalene rings, and anthracene rings. The aromatic hydrocarbon may have a substituent. Examples of the substituent include a halogen atom, a hydroxy group, an alkyl group in which the carbon atoms are in a range of 1 to 6, and an alkoxy group in which the carbon atoms are in a range of 1 to 6. The carbonyl group may be directly bonded to the aromatic hydrocarbon or may be bonded via an alkylene group in which the carbon atoms are in a range of 1 to 6. Specific examples of the aromatic carbonyl compound include benzalacetone, cinnamic acid, cinnamaldehyde, and benzaldehyde.

The aromatic carbonyl compounds may be used alone as one type or in a combination of two or more types. The amount of the aromatic carbonyl compound in the tin alloy plating solution of the first embodiment is generally in a range of 0.01 mg/L or more and 500 mg/L or less, preferably in a range of 0.1 mg/L or more and 100 mg/L or less, and more preferably in a range of 1 mg/L or more and 50 mg/L or less.

Second Embodiment

The tin alloy plating solution of the second embodiment includes a soluble tin salt, a soluble salt of a metal which is more noble than tin, and the sulfide compound represented by General Formula (2). This tin alloy plating solution may further include an additive.

The soluble tin salt, the soluble salt of a metal which is more noble than tin, and the additives included in the tin alloy plating solution of the second embodiment are the same as the soluble tin salt, the soluble salt of a metal which is more noble than tin, and the additive included in the tin alloy plating solution of the first embodiment, thus, a repeated description thereof will be omitted.

[Sulfide Compound Represented by General Formula (2)]

The sulfide compound used in the tin alloy plating solution of the second embodiment is represented by General Formula (2) and acts as a complexing agent for the metal which is more noble than tin. This sulfide compound is obtained by mixing α-thioglycerol as a main raw material with, for example, a basic aqueous solution such as sodium hydroxide, sodium hydrogen carbonate, or sodium carbonate, then mixing and stirring the auxiliary raw materials described below, and then carrying out refluxing to subject the main raw material and the auxiliary raw materials to a nucleophilic substitution reaction. The amount of the sulfide compound in the tin alloy plating solution of the second embodiment is the same as the amount of the sulfide compound in the tin alloy plating solution of the first embodiment. A method for producing the sulfide compound of Example 15 described below will be illustrated. 200 mL of pure water and 200 mL of ethanol as a solvent are prepared in a 2 L eggplant-shaped flask, and 112 g of potassium hydroxide is dissolved therein while stirring. After cooling the solution to 25° C., 216 g of α-thioglycerol is added thereto and mixed therein. Then, 113 g of 1,3-dichloropropane is added as an auxiliary raw material and mixed therein. After refluxing at 80° C. for 24 hours, the solvent is removed by distillation to obtain a sulfide compound represented by Structural Formula (2-2) described below.

Examples of auxiliary raw materials for producing the sulfide compound of the second embodiment include dichloromethane, 1,3-dichloropropane, 1,4-dichlorobutane, 1,3-dichloro-2-propanol, 1,4-dichloro-2-butanol, 1,4-dichloro-2,3-butanediol, and the like.

Third Embodiment

The tin alloy plating solution of the third embodiment includes a soluble tin salt, a soluble salt of a metal which is more noble than tin, and a sulfide compound represented by General Formula (3). This tin alloy plating solution may further include an additive.

The soluble tin salt, the soluble salt of a metal which is more noble than tin, and the additives included in the tin alloy plating solution of the third embodiment are the same as the soluble tin salt, the soluble salt of a metal which is more noble than tin, and the additive included in the tin alloy plating solution of the first embodiment, thus, a repeated description thereof will be omitted.

[Sulfide Compound Represented by General Formula (3)]

The sulfide compound used in the tin alloy plating solution of the third embodiment is represented by General Formula (3) and acts as a complexing agent for the metal which is more noble than tin. This sulfide compound is obtained by mixing α-thioglycerol as a main raw material with, for example, a basic aqueous solution such as sodium hydroxide, sodium hydrogen carbonate, or sodium carbonate, then mixing and stirring the auxiliary raw materials described below, and then carrying out refluxing to subject the main raw material and the auxiliary raw materials to a reaction. The amount of the sulfide compound in the tin alloy plating solution of the third embodiment is the same as the amount of the sulfide compound in the tin alloy plating solution of the first embodiment. A method for producing the sulfide compound of Example 20 described below will be illustrated. 200 mL of pure water and 200 mL of ethanol as a solvent are prepared in a 2 L eggplant-shaped flask, and 168 g of sodium hydrogen carbonate is dissolved therein while stirring. After cooling the solution to 25° C., 216 g of α-thioglycerol is added thereto and mixed therein. Then, 143 g of bis(2-chloroethyl)ether is added as an auxiliary raw material and mixed therein. After refluxing at 80° C. for 48 hours, the solvent is removed by distillation to obtain a sulfide compound represented by Structural Formula (3-1) described below.

Examples of auxiliary raw materials for producing the sulfide compound of the third embodiment include bis(2-chloroethyl)ether, 1,2-bis(2-chloroethoxy)ethane, diethylene glycol bis(2-chloroethyl)ether, bis[2-[2-(2-chloroethoxy)ethoxy]ethyl] ether, and the like.

The amount of the sulfide compound in the tin alloy plating solution of the first, second, and third embodiments is preferably 0.5 or more in a molar ratio with respect to the amount of the metal which is more noble than tin in the plating solution (amount (mol) of the sulfide compound/amount (mol) of metal which is more noble than tin). The molar ratio is preferably one or more. When the molar ratio is less than 0.5, the complex formation is insufficient between the sulfide compound and the metal which is more noble than tin in the plating solution and there is a concern that the concentration of the metal which is more noble than tin in the plating solution may decrease. The upper limit of the molar ratio is not particularly limited, but is preferably 100 or less. It is uneconomical to contain a sulfide compound such that the molar ratio exceeds 100. The sulfide compounds illustrated in the first, second, and third embodiments described above may be used in a combination of a plurality of types.

It is possible to analyze the structures of the sulfide compounds in the tin alloy plating solutions of the first, second, and third embodiments by using an analytical instruments for high-performance liquid chromatography (HPLC), a high-performance liquid chromatogram mass spectrometer (LC-MS), Fourier transform infrared spectroscopy (FT-IR), a nuclear magnetic resonance device (NMR), or the like.

It is possible to prepare the tin alloy plating solutions of the first, second, and third embodiments, for example, by mixing soluble tin salts, soluble salts of metals which are more noble than tin, the sulfide compound represented by General Formula (1), General Formula (2), or General Formula (3), and the other components with water. In order to suppress the oxidation of $Sn^{2+}$ ions and a reduction reaction with the metal ion which is more noble than tin, it is preferable to mix the soluble salt of a metal which is more noble than tin after adding the sulfide compound.

As a method for forming a plating film using the plating solutions of the first, second, and third embodiments, electroplating is used as described above. The current density at the time of forming a plating film by electroplating is in a range of 0.1 $A/dm^2$ or more and 100 $A/dm^2$ or less, and preferably 0.5 $A/dm^2$ or more and 20 $A/dm^2$ or less. While electroplating is performed, the solution temperature of the plating solution is in a range of 10° C. or higher and 50° C. or lower, and more preferably 20° C. or higher and 40° C. or lower.

EXAMPLES

Next, a detailed description will be given of Examples of the present invention together with Comparative Examples.
<Sulfide Compounds Used in Examples 1 to 13 and Comparative Examples 1 to 3>

First, the main raw materials and auxiliary raw materials for producing the sulfide compounds described in the first embodiment used in Examples 1 to 13 and Comparative Examples 1 to 3 and the reference numerals of the structural formulas of the produced sulfide compounds are shown in Table 1. In addition, the structural formulas are listed below. The sulfide compounds used in Examples 1 to 13 and Comparative Examples 1 to 3 were produced by the method described in the first embodiment.

TABLE 1

| | | | Sulfide compound | | |
|---|---|---|---|---|---|
| | Main raw material | Auxiliary raw material | Structural Formula | Number of oxygen atoms | Number of carbon atoms |
| Example 1 | α-thioglycerol | Chloromethane | (1-1) | 0 | 1 |
| Example 2 | α-thioglycerol | Chloroethane | (1-2) | 0 | 2 |
| Example 3 | α-thioglycerol | 2-chloroethanol | (1-3) | 1 | 2 |
| Example 4 | α-thioglycerol | 3-chloro-1-propanol | (1-4) | 1 | 3 |
| Example 5 | α-thioglycerol | 1-chloro-3-methaoxypropane | (1-5) | 1 | 4 |
| Example 6 | α-thioglycerol | 3-chloro-1,2-propanediol | (1-6) | 2 | 3 |
| Example 7 | α-thioglycerol | 2-(2-chloroethoxy)ethanol | (1-7) | 2 | 4 |
| Example 8 | α-thioglycerol | 1-chloro-3-methoxy-2-propanol | (1-8) | 2 | 4 |
| Example 9 | α-thioglycerol | 2-[2-(2-chloroethoxy)ethoxy]ethanol | (1-9) | 3 | 6 |
| Example 10 | α-thioglycerol | Dimethylchloroacetal | (1-10) | 2 | 4 |
| Example 11 | α-thioglycerol | 4-chloro-1,2-dihydroxybenzene | (1-11) | 2 | 6 |
| Example 12 | α-thioglycerol | Chloromethane | (1-1) | 0 | 1 |
| Example 13 | α-thioglycerol | Chloromethane | (1-1) | 0 | 1 |
| Comparative Example 1 | — | — | (1-12) | 0 | 0 |

TABLE 1-continued

|  | Main raw material | Auxiliary raw material | Sulfide compound | | |
|---|---|---|---|---|---|
|  |  |  | Structural Formula | Number of oxygen atoms | Number of carbon atoms |
| Comparative Example 2 | α-thioglycerol | Isopropylchloride | (1-13) | 0 | 3 |
| Comparative Example 3 | — | — | (1-14) | — | — |

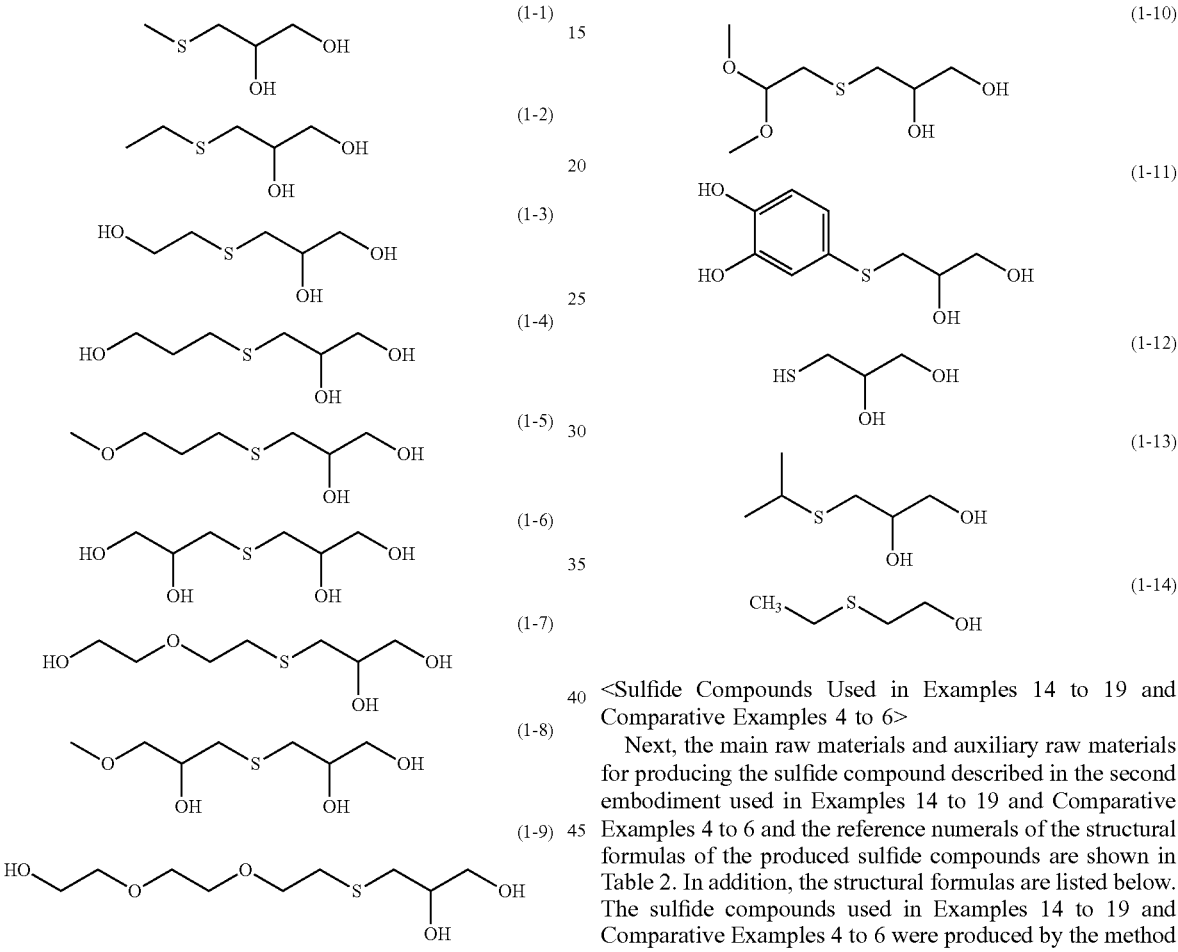

<Sulfide Compounds Used in Examples 14 to 19 and Comparative Examples 4 to 6>

Next, the main raw materials and auxiliary raw materials for producing the sulfide compound described in the second embodiment used in Examples 14 to 19 and Comparative Examples 4 to 6 and the reference numerals of the structural formulas of the produced sulfide compounds are shown in Table 2. In addition, the structural formulas are listed below. The sulfide compounds used in Examples 14 to 19 and Comparative Examples 4 to 6 were produced by the method described in the second embodiment.

TABLE 2

|  | Main raw material | Auxiliary raw material | Sulfide compound | | |
|---|---|---|---|---|---|
|  |  |  | Structural Formula | Number of oxygen atoms | Number of carbon atoms |
| Example 14 | α-thioglycerol | Dichloromethane | (2-1) | 0 | 1 |
| Example 15 | α-thioglycerol | 1,3-dichloropropane | (2-2) | 0 | 3 |
| Example 16 | α-thioglycerol | 1,4-dichlorobutane | (2-3) | 0 | 4 |
| Example 17 | α-thioglycerol | 1,3-dichloro-2-propanol | (2-4) | 1 | 3 |
| Example 18 | α-thioglycerol | 1,4-dichloro-2-butanol | (2-5) | 1 | 4 |
| Example 19 | α-thioglycerol | 1,4-dichloro-2,3-butanediol | (2-6) | 2 | 4 |
| Comparative Example 4 | α-thioglycerol | α-thioglycerol | (2-7) | 0 | 0 |
| Comparative Example 5 | α-thioglycerol | 1,5-dichloropentane | (2-8) | 0 | 5 |

TABLE 2-continued

| | Main raw material | Auxiliary raw material | Sulfide compound Structural Formula | Number of oxygen atoms | Number of carbon atoms |
|---|---|---|---|---|---|
| Comparative Example 6 | — | — | (2-9) | — | — |

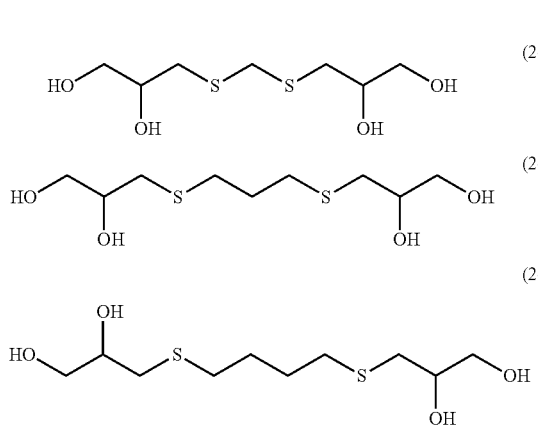

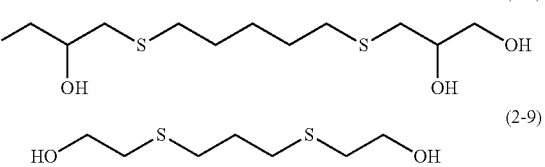

<Sulfide Compounds Used in Examples 20 to 23>

Further, the main raw materials and auxiliary raw materials for producing the sulfide compounds described in the third embodiment used in Examples 20 to 23 and the reference numerals of the structural formulas of the produced sulfide compounds are shown in Table 3. In addition, the structural formulas are listed below. The sulfide compounds used in Examples 20 to 23 were produced by the method described in the third embodiment.

TABLE 3

| | Main raw material | Auxiliary raw material | Sulfide compound Structural Formula | n |
|---|---|---|---|---|
| Example 20 | α-thioglycerol | Bis(2-chloroethyl)ether | (3-1) | 1 |
| Example 21 | α-thioglycerol | 1,2-bis(2-chloroethoxy)ethane | (3-2) | 2 |
| Example 22 | α-thioglycerol | Diethyleneglycolbis(2-chloroethyl)ether | (3-3) | 3 |
| Example 23 | α-thioglycerol | Bis[2-[2-(2-chloroethoxy)ethoxy]ethyl]ether | (3-4) | 5 |

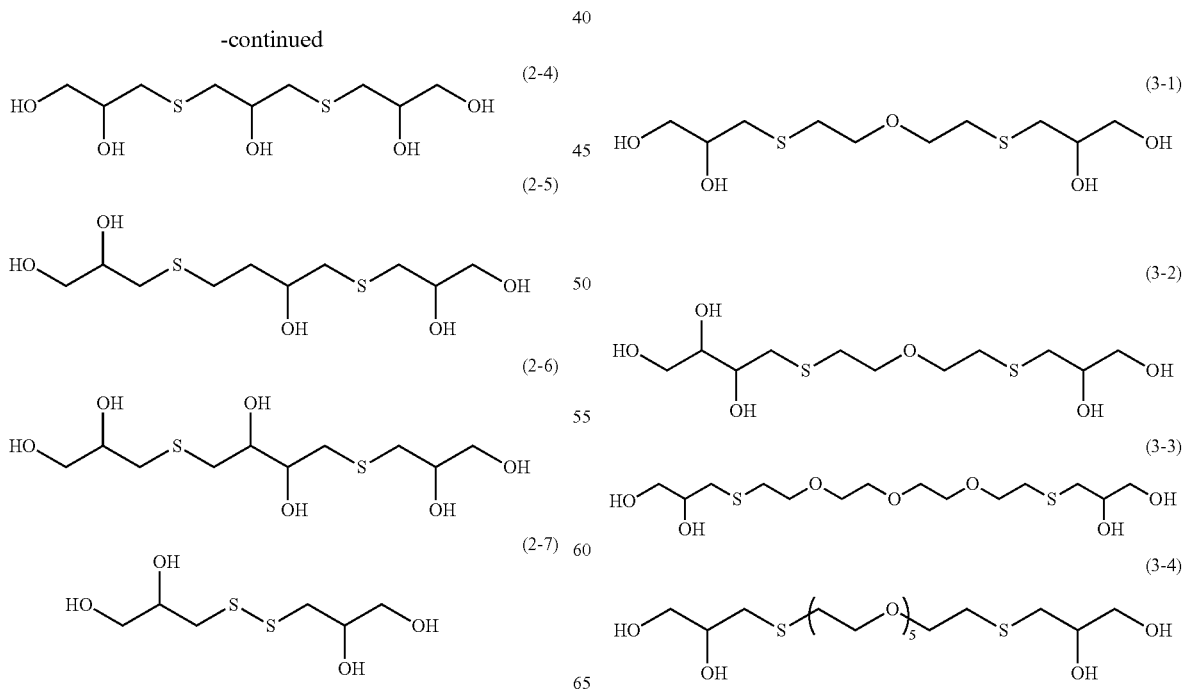

(Vat of SnAg Plating Solution)

Example 1

Methane sulfonic acid as a free acid, a sulfide compound of Structural Formula (1-1), a non-ionic surfactant (in which polyoxyethylene and polyoxypropylene were added to ethylenediamine at a ratio of 50:50), and pyrogallol as an antioxidant were mixed and dissolved in an aqueous solution of tin methane sulfonic acid, and then an aqueous solution of silver methane sulfonic acid was added thereto and mixed therewith. Finally, by adding ion-exchanged water thereto, a SnAg plating solution having the following composition was vatted. The molar ratio of the sulfide compound with respect to the Ag amount in the SnAg plating solution having the following composition was 1. The aqueous solution of tin methane sulfonic acid was prepared by electrolyzing a metal tin plate, and the aqueous solution of silver methane sulfonic acid was prepared by electrolyzing a metal silver plate, both in an aqueous solution of methane sulfonic acid.
(Composition of SnAg Plating Solution)
Tin methane sulfonic acid (as $Sn^{2+}$): 50 g/L
Silver methane sulfonic acid (as $Ag^+$): 0.5 g/L
Methane sulfonic acid (as free acid): 150 g/L
Amount (molar ratio) of sulfide compound (Structural Formula (1-1)): 1
Non-ionic surfactant: 5 g/L
Antioxidant: 1 g/L
Ion-exchanged water: remainder

Examples 2 to 11

In Examples 2 to 11, the sulfide compounds of Structural Formulas (1-2) to (1-11) were used, respectively. In Examples 2 to 11, each SnAg plating solution was vatted in the same manner as in Example 1 except that the sulfide compounds were each changed.

Example 12

In Example 12, the same sulfide compound of Structural Formula (1-1) was used as in Example 1. In Example 12, the molar ratio of the sulfide compound with respect to the Ag amount in the SnAg plating solution was 100. A SnAg plating solution was vatted in the same manner as in Example 1 except that this molar ratio was changed.

Example 13

In Example 13, the same sulfide compound of Structural Formula (1-1) was used as in Example 1. In Example 13, copper methane sulfonic acid was used instead of silver methane sulfonic acid to prepare an SnCu alloy plating solution. In addition, a plating solution was vatted in the same manner as in Example 1 except that the alloy type was changed.

Comparative Example 1

In Comparative Example 1, for comparison with Example 1, the sulfide compound (α-thioglycerol) of Structural Formula (1-12) in which both the number of oxygen atoms and the number of carbon atoms in (A) in General Formula (1) were zero was used. Other than this, the SnAg plating solution was vatted in the same manner as in Example 1.

Comparative Example 2

In Comparative Example 2, for comparison with Example 2, a sulfide compound of Structural Formula (1-13) in which the number of oxygen atoms was zero and the number of carbon atoms was 3 in (A) in General Formula (1) was used. In this Structural Formula (1-13), the number of oxygen atoms was zero and the number of carbon atoms was 3. Other than this, the SnAg plating solution was vatted in the same manner as in Example 1.

Comparative Example 3

In Comparative Example 3, for comparison with Example 2, a sulfide compound (2-(ethylthio)ethanol) of Structural Formula (1-14) different from General Formula (1) was used. Other than this, the SnAg plating solution was vatted in the same manner as in Example 1.

Examples 14 to 19

In Examples 14 to 19, sulfide compounds of Structural Formulas (2-1) to (2-6) were used, respectively. In Examples 14 to 19, each SnAg plating solution was vatted in the same manner as in Example 1 except that the sulfide compound was changed.

Comparative Example 4

In Comparative Example 4, for comparison with Example 14, a sulfide compound of Structural Formula (2-7) in which both the number of oxygen atoms and the number of carbon atoms in (B) in General Formula (2) were zero was used. Other than this, the SnAg plating solution was vatted in the same manner as in Example 1.

Comparative Example 5

In Comparative Example 5, for comparison with Example 16, a sulfide compound of Structural Formula (2-8) in which the number of oxygen atoms was zero and the number of carbon atoms was 5 in (B) in General Formula (2) was used. Other than this, the SnAg plating solution was vatted in the same manner as in Example 1.

Comparative Example 6

In Comparative Example 6, for comparison with Example 15, a sulfide compound (3,7-dithia-1,9-nonanediol) of Structural Formula (2-9) different from General Formula (2) was used. Other than this, the SnAg plating solution was vatted in the same manner as in Example 1.

Examples 20 to 23

In Examples 20 to 23, the sulfide compounds of Structural Formulas (3-1) to (3-4) were used, respectively. In Examples 20 to 23, a SnAg plating solution was vatted in the same manner as in Example 1 except that the sulfide compound was changed.

The amounts (molar ratios) of each sulfide compound with respect to the Ag amount in the SnAg plating solution in Examples 1 to 23 and Comparative Examples 1 to 6 are shown in Tables 4 and 5 below.

<Comparison Test and Evaluation>

For the 29 types of Examples 1 to 23 and Comparative Examples 1 to 6, the transparency of the tin alloy plating solutions immediately after being vatted and the stability of the tin alloy plating solutions which were vatted were evaluated. The stability of the tin alloy plating solution was evaluated by performing an aging stability test and an electrolytic stability test. The results are shown in Tables 4 and 5.

(a) Transparency

Immediately after being vatted, the 29 types of tin alloy plating solution were put in a transparent glass beaker and the transparency was visually observed. A beaker in which the plating solution was transparent was determined to be "transparent", and a beaker in which the plating solution became cloudy was determined to be "cloudy".

(b) Aging Stability Test

The 29 types of tin alloy plating solutions which were vatted were placed in glass sealed bottles separately and stored in a clean oven made by Panasonic at 50° C. for 6 months. Using an ICP atomic emission spectrometer (ICP-AES, model number ICPE-9800) manufactured by Shimadzu Corporation, the Ag concentration (in the case of an SnAg plating solution) or the Cu concentration (in the case of an SnCu plating solution) in the tin alloy plating solution immediately after being vatted was set as 100% and the residual proportion (%) of the Ag concentration (in the case of the SnAg plating solution) or the Cu concentration (in the case of the SnCu plating solution) remaining in the tin alloy plating solution after storage for 6 months was evaluated as the "residual proportion after aging". 80% or more was determined to be good.

(c) Electrolytic Stability Test

The 29 types of tin alloy plating solution which were vatted were used as an electrolytic solution, a copper plate and a platinum plate were arranged in the electrolytic solution as a cathode and as an anode respectively, and electroplating was performed separately for the 29 types of tin alloy plating solutions which were vatted at a vat temperature of 25° C. and a cathode current density of 10 ASD. Since metal components in the plating solution were consumed by electrolytic plating, stannous oxide (SnO) and silver oxide ($Ag_2O$) powders were added, mixed, and dissolved in the plating solution every 5 Ah/L of electrolytic plating such that the electrolytic plating was performed up to 150 Ah/L while replenishing the metal component in the plating solution. The concentration of the sulfide compound remaining in the tin alloy plating solution after electrolytic plating was quantitatively analyzed by the following high-performance liquid chromatography (HPLC) method. The tin alloy plating solution was filtered with a disposable syringe and analyzed using an HPLC device (model: Prominence) manufactured by Shimadzu Corporation, using L-Column ODS kept at 40° C. with a mobile phase of MeOH (methanol). With the concentration of the sulfide compound immediately after being vatted being set as 100%, the residual proportion (%) of the sulfide compound after electrolytic plating was evaluated as the "residual proportion after aging" of the complexing agent. 80% or more was determined to be good.

TABLE 4

|  | Amount of sulfide compound (molar ratio) | Transparency | Residual proportion after aging (%) | Residual proportion after electrolysis (%) |
|---|---|---|---|---|
| Example 1 | 1 | Transparent | 95 | 94 |
| Example 2 | 1 | Transparent | 91 | 82 |
| Example 3 | 1 | Transparent | 97 | 88 |
| Example 4 | 1 | Transparent | 98 | 94 |
| Example 5 | 1 | Transparent | 96 | 92 |
| Example 6 | 1 | Transparent | 98 | 99 |
| Example 7 | 1 | Transparent | 93 | 90 |
| Example 8 | 1 | Transparent | 98 | 90 |
| Example 9 | 1 | Transparent | 96 | 95 |
| Example 10 | 1 | Transparent | 97 | 89 |
| Example 11 | 1 | Transparent | 87 | 83 |
| Example 12 | 100 | Transparent | 96 | 98 |
| Example 13 | 1 | Transparent | 89 | 92 |
| Comparative Example 1 | 1 | Transparent | Evaluation not possible | Evaluation not possible |
| Comparative Example 2 | 1 | Cloudy | 83 | 68 |
| Comparative Example 3 | 1 | Transparent | 54 | 38 |

TABLE 5

|  | Amount of sulfide compound (molar ratio) | Transparency | Residual proportion after aging (%) | Residual proportion after electrolysis (%) |
|---|---|---|---|---|
| Example 14 | 1 | Transparent | 97 | 83 |
| Example 15 | 1 | Transparent | 94 | 87 |
| Example 16 | 1 | Transparent | 90 | 91 |
| Example 17 | 1 | Transparent | 98 | 87 |
| Example 18 | 1 | Transparent | 95 | 93 |
| Example 19 | 1 | Transparent | 99 | 97 |
| Comparative Example 4 | 1 | Cloudy | Evaluation not possible | Evaluation not possible |
| Comparative Example 5 | 1 | Transparent | 80 | 72 |
| Comparative Example 6 | 1 | Transparent | 68 | 56 |
| Example 20 | 1 | Transparent | 92 | 89 |

TABLE 5-continued

| | Amount of sulfide compound (molar ratio) | Transparency | Residual proportion after aging (%) | Residual proportion after electrolysis (%) |
|---|---|---|---|---|
| Example 21 | 1 | Transparent | 94 | 90 |
| Example 22 | 1 | Transparent | 94 | 92 |
| Example 23 | 1 | Transparent | 95 | 94 |

As is clear from Table 1 and Table 4, in Comparative Example 1 using a compound in which (A) in General Formula (1) did not meet the conditions of the first aspect of the present invention, the SH group of the terminal group of the compound reacted with Ag immediately after being vatted to generate a precipitate and evaluation after aging and after electrolytic plating was not possible. In Comparative Example 2 using a sulfide compound in which (A) in General Formula (1) did not meet the conditions of the first aspect of the present invention, the number of carbon atoms was 3, thus, the water solubility of the sulfide compound was low and the residual proportion after aging was 83%, but the residual proportion after electrolysis was as low as 68%, which was unsatisfactory. In addition, in Comparative Example 3 in which the sulfide compound (2-(ethylthio) ethanol) of Structural Formula (1-14) different from General Formula (1) was used, the water solubility of the sulfide compound was low, the residual proportion after aging was 54%, and the residual proportion after electrolysis was as low as 38%, which was unsatisfactory.

On the other hand, in Examples 1 to 13 using the sulfide compound in which (A) in General Formula (1) met the conditions of the first aspect of the present invention, the residual proportion of Ag and Cu in the plating solution after aging was as high as 87% to 98% and the sulfide compound also remained at a high ratio of 82% to 99% after electrolytic plating. From these results, it was confirmed that the sulfide compound in which (A) in General Formula (1) met the conditions of the first aspect of the present invention was useful as a complexing agent for metals which are more noble than tin.

As is clear from Table 2 and Table 5, in Comparative Example 4 in which (B) in General Formula (2) did not meet the conditions of the second aspect of the present invention, the disulfide group of the sulfide compound reacted with Ag immediately after being vatted to generate a precipitate and evaluation after aging and after electrolytic plating was not possible. In Comparative Example 5 using the sulfide compound in which (B) in General Formula (2) did not meet the conditions of the second aspect of the present invention, since the carbon chain was 5, the water solubility of the sulfide compound was low and the residual proportion after aging was 80%, but the residual proportion after electrolysis was as low as 72%, which was unsatisfactory. In addition, in Comparative Example 6 of Structural Formula (2-9) different from General Formula (2) of the second aspect of the present invention, since the sulfide compound did not have a glyceryl group, the water solubility of the sulfide compound was low, the residual proportion after aging was 68%, and the residual proportion after electrolysis was 56%, which were both low and unsatisfactory.

On the other hand, in Examples 14 to 19 using the sulfide compound in which (B) in General Formula (2) met the conditions of the second aspect of the present invention, after aging, the residual proportion of Ag in the SnAg plating solution was as high as 90% to 99%, and the sulfide compound also remained at a high ratio of 83% to 97% after electrolytic plating. From these results, it was confirmed that the sulfide compound in which (B) in General Formula (2) met the conditions of the second aspect of the present invention was useful as a complexing agent for metals which are more noble than tin.

As is clear from Tables 3 and 5, in Examples 20 to 23 using the sulfide compound which met the conditions of the third aspect of the present invention in which n in General Formula (3) was 1 to 5, after aging, the residual proportion of Ag in the SnAg plating solution was as high as 92% to 95% and the sulfide compound also remained at a high ratio of 89% to 94% after electrolytic plating. From these results, it was confirmed that the sulfide compound which met the condition of the third aspect of the present invention, in which n in General Formula (3) is 1 to 5, was useful as a complexing agent for metals which are more noble than tin.

INDUSTRIAL APPLICABILITY

It is possible to use the plating solution of the present invention to form parts of electronic components such as bump electrodes of semiconductor wafers and printed circuit boards.

What is claimed is:
1. A tin alloy plating solution comprising:
a soluble tin salt;
a soluble salt of a metal which is more noble than tin; and
a sulfide compound represented by General Formula (3), here, in the General Formula (3), n is 1 to 5

(3)

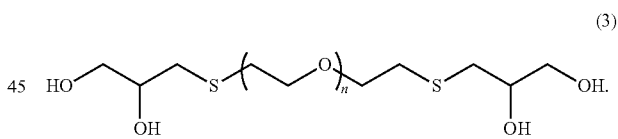

2. The tin alloy plating solution according to claim 1, wherein the metal which is more noble than tin is at least one or more metals selected from silver, copper, gold, and bismuth.
3. The tin alloy plating solution according to claim 2, further comprising at least one or more types of auxiliary complexing agent selected from a gluconic acid or a salt thereof, a citric acid or a salt thereof, a pyrophosphoric acid or a salt thereof, an ethylenediamine, a thiourea, a mercaptothiazole, a mercaptotriazole, a mercaptotetrazole, and a hydroxyalkylphosphine.
4. The tin alloy plating solution according to claim 2, further comprising at least one or more types of surfactant selected from an anionic surfactant, a cationic surfactant, a non-ionic surfactant, and an amphoteric surfactant.
5. The tin alloy plating solution according to claim 2, further comprising an antioxidant.
6. The tin alloy plating solution according to claim 2, further comprising a complexing agent for tin.

7. The tin alloy plating solution according to claim 1, further comprising at least one or more types of auxiliary complexing agent selected from a gluconic acid or a salt thereof, a citric acid or a salt thereof, a pyrophosphoric acid or a salt thereof, an ethylenediamine, a thiourea, a mercaptothiazole, a mercaptotriazole, a mercaptotetrazole, and a hydroxyalkylphosphine.

8. The tin alloy plating solution according to claim 7, further comprising at least one or more types of surfactant selected from an anionic surfactant, a cationic surfactant, a non-ionic surfactant, and an amphoteric surfactant.

9. The tin alloy plating solution according to claim 7, further comprising an antioxidant.

10. The tin alloy plating solution according to claim 7, further comprising a complexing agent for tin.

11. The tin alloy plating solution according to claim 1, further comprising at least one or more types of surfactant selected from an anionic surfactant, a cationic surfactant, a non-ionic surfactant, and an amphoteric surfactant.

12. The tin alloy plating solution according to claim 11, further comprising an antioxidant.

13. The tin alloy plating solution according to claim 11, further comprising a complexing agent for tin.

14. The tin alloy plating solution according to claim 1, further comprising an antioxidant.

15. The tin alloy plating solution according to claim 14, further comprising a complexing agent for tin.

16. The tin alloy plating solution according to claim 1, further comprising a complexing agent for tin.

17. The tin alloy plating solution according to claim 1, further comprising a pH adjusting agent.

18. The tin alloy plating solution according to claim 1, further comprising a brightening agent.

* * * * *